United States Patent [19]

Kost et al.

[11] Patent Number: 4,780,212

[45] Date of Patent: Oct. 25, 1988

[54] ULTRASOUND ENCHANCEMENT OF MEMBRANE PERMEABILITY

[75] Inventors: Joseph Kost, Omer, Israel; Robert S. Langer, Somerville, Mass.

[73] Assignee: Massachusetts Institute of Technology, Cambridge, Mass.

[21] Appl. No.: 80,325

[22] Filed: Jul. 31, 1987

[51] Int. Cl.⁴ ............................................. B01D 13/00
[52] U.S. Cl. .................................... 210/646; 204/152; 210/651; 210/652; 210/748
[58] Field of Search ............... 210/651, 650, 652, 649, 210/748, 645–647; 204/180, 186, 149, 152

[56] References Cited

U.S. PATENT DOCUMENTS 4,078,052  3/1978  Papahadjopoulos .
4,280,623  7/1981  Legorreta .
4,309,989  1/1982  Fahim .
4,591,496  5/1986  Cohen et al. .

FOREIGN PATENT DOCUMENTS 8293568  10/1982  World Int. Prop. O. .

OTHER PUBLICATIONS

Griffin, *J. Amer. Phys. Therapy Association* 46, 18–26 (1966).
Dyson, et al., *Ultrasonics* 232–235 (Sep. 1976).
Lenart, et al., *Ultrasonics* 216–218 (Sep. 1980).
J. Lehmann, et al., "Uber die Wirkung von Ultraschall-Wellen auf den Ionendurchtritt durch biologische Membranen als Beitrag zur Theorie des therapeutischen Wirkungsmechanismus", 311–318.
Skauen and Zentner, *Int. Journal Pharmaceutics* 20, 235–245 (1984).
Brochure on the Sonopuls 434 ultrasound therapeutic apparatus.

*Primary Examiner*—Frank Sever
*Attorney, Agent, or Firm*—Kilpatrick & Cody

[57] ABSTRACT

A method for enhancing or controlling permeability of large molecular weight molecules in a membrane system wherein molecules in solution are contacted with membranes and the system is exposed to ultrasound at a selected intensity and frequency and for a specific length of time. The method may be designed to insure that only reversible changes in the membrane result from exposure to the ultrasound or to enhance the rate of degradation of the membrane and/or selectivity of passage of molecules through the membrane. The method may include selection of the membrane composition and structure, including the pore size, thickness, crystallinity and molecular arrangement. Selection of the solvent or media in which the molecules are suspended may be used to further enhance or control permeability. The media may be either an aqueous or inorganic solution with the physical and chemical properties may be selected to attenuate sound transmission or to enhance stability of the molecule permeating the membrane.

20 Claims, 2 Drawing Sheets

ULTRASOUND ENCHANCEMENT OF MEMBRANE PERMEABILITY

The Government has rights in this invention pursuant to Grant Number NIH-2-R01-GM26698-07 awarded by the Department of Health and Human Services.

BACKGROUND OF THE INVENTION

The present invention is generally in the field of ultrasound and specifically in the areas of alteration of membrane permeability and molecule-molecule interaction by ultrasound.

Ultrasound has been used for a variety of chemical applications. For example, ultrasound has been used to make phospholipid vesicles, as described in U.S. Pat. No. 4,078,052 to Papahadjopoulos, and to orient cells in a liquid flow cell analyzer apparatus, as described in U.S. Pat. No. 4,280,623 to Legorreta. Ultrasound has been used in apparatus for cleaning objects such as jewelry in the presence of a surfactant.

Ultrasound has also been used in a number of medical applications. An early review of the clinical use of ultrasound for the treatment of soft tissue injury or pain is described by James E. Griffen in "Physiological Effects of Ultrasonic Energy as it is Used Clinically", *J. Amer. Phys. Therapy Assoc.* 46, 18–26 (1966). One example of a clinical application of ultrasound has been to stimulate healing of soft tissue, as described by "Stimulation of Healing of Varicose Ulcers by Ultrasound" by M. Dyson et. al. in *Ultrasonics,* 232–235 (Sept. 1976). Ultrasound has also been described in U.S. Pat. No. 4,309,989 to Fahim as useful in the topical application of a medication, and for enhancement of transdermal drug delivery into the circulatory system, as described in U.S. patent application Ser. No. 883,111 filed July 8, 1986 by Joseph Kost, Drora Levy and Robert S. Langer entitled "Ultrasound Enhancement of Transdermal Drug Delivery". U.S. patent application Ser. No. 633,366 filed July 23, 1984, and the divisional U.S. Ser. No. 936,000 filed Nov. 28, 1986 by Joseph Kost and Robert S. Langer entitled "Ultrasonically Modulated Polymeric Devices for Delivering Compositions" disclose a process for delivering a drug from within a polymeric matrix utilizing an external source of ultrasonic energy. The ultrasonic energy degrades the polymeric matrix to effect release of the composition incorporated into the polymeric matrix. The advantage of this process is that the rate of release from the polymeric matrix can be controlled externally when the device is implanted in vivo.

Ultrasound has also been used to affect the diffusion of electrolytes through a cellophane membrane, described by I. Lenart and D. Auslander in "The Effect of Ultrasound on Diffusion through Membranes", *Ultrasonics,* 216–218 (Sept. 1980), and a biological membrane, described by J. Lehmann et. al., in "Uber die Wirkung von Ultraschall-Wellen auf den Ionendurchtritt durch biologische Membranen als Beitrag zur Theorie dis Therapeutischen Wirkungs-mechanismus" 311–318. Enhanced passage of ions and small molecules through cellophane membranes and frog skin is reported in "Phonophoresis" by D. M. Skauen and G. M. Zentner in *Int. J. Pharm.* 20, 235–245 at 238–239 (1984).

In general, none of these processes provide a means for controlling the passage of large or complex molecules suspended or dissolved in a liquid media through a membrane. Further, none of these processes alter the relationship of the molecule with its immediate environment, either a membrane or molecule of the same composition, for example, as in a molecular aggregate. Even those articles which discuss enhanced passage of topical compositions through the skin and treatment of soft tissue and connective tissue injury focus on the use of the ultrasound to generate heat while noting that the mechanisms by which these processes are controlled are unclear.

It is therefore an object of the present invention to provide a method for altering permeability of a membrane to molecules wherein the alteration is totally reversible and can be controlled as to the extent and rate of alteration.

It is a further object of the present invention to provide a method for selectively altering membrane permeability to molecules.

It is another object of the present invention to provide a method for dispersing molecular aggregates or physical complexes of molecules, particularly proteins in an aqueous solution.

SUMMARY OF THE INVENTION

The present invention is the use of ultrasound to control the relationship of a molecule to the other molecules in its immediate environment. Specifically, two applications are disclosed: the alteration of membrane permeability to a particular molecule(s) and dispersion of physical aggregates of molecules.

The method using ultrasound to control transport or permeability of molecules through polymeric or biological membranes is dependent on the control of a number of factors in addition to the frequency, intensity and time of exposure to ultrasound. For example, the composition and structure, including pore size, thickness, crystallinity, and molecular arrangement, of the membrane can be selected which produce the desired rate of passage of the molecules through the membrane on exposure to ultrasound. The media in which the molecules are suspended can also be selected for particular physical and chemical characteristics, including viscosity and sound attenuation, which will produce the desired rate of permeation through the membrane in response to the ultrasound. In some cases where the media is not to be altered, the thickness of the solution is decreased appropriately.

The frequency and intensity of the ultrasound, as well as the duration of exposure, are controlled according to the nature and composition of the molecules and membrane, as well as the rate of permeation and desired final concentration. In general, the intensity, frequency and exposure will be limited to produce reversible changes. The power will preferably be within the range of approximately 0.05 to 30 watts/cm$^2$, and preferably less than 5 watts/cm$^2$ for biological membranes. The frequency is generally set between about 10 kHz and 20 MHz, preferably between 1 MHz and 3 MHz for biological membranes, with the desired frequency being proportional to the intensity. Pulsing can be used to decrease the amount of heat generated over time at a particular intensity. Times of less than five or ten minutes are preferred for biological systems to avoid irreversible damage to the membrane.

The system is exceedingly flexible and can be designed to accommodate variations in the membrane, the number, size and properties of the molecules passing through the membrane, the media in which the molecules are suspended, the location of the ultrasonic source, the total length of time over which the molecule is to pass through the membrane, and whether or not the membrane is simultaneously degrading both as a function of the exposure to the ultrasound as well as to chemical breakdown over time.

DETAILED DESCRIPTION OF THE INVENTION

Figure 1:
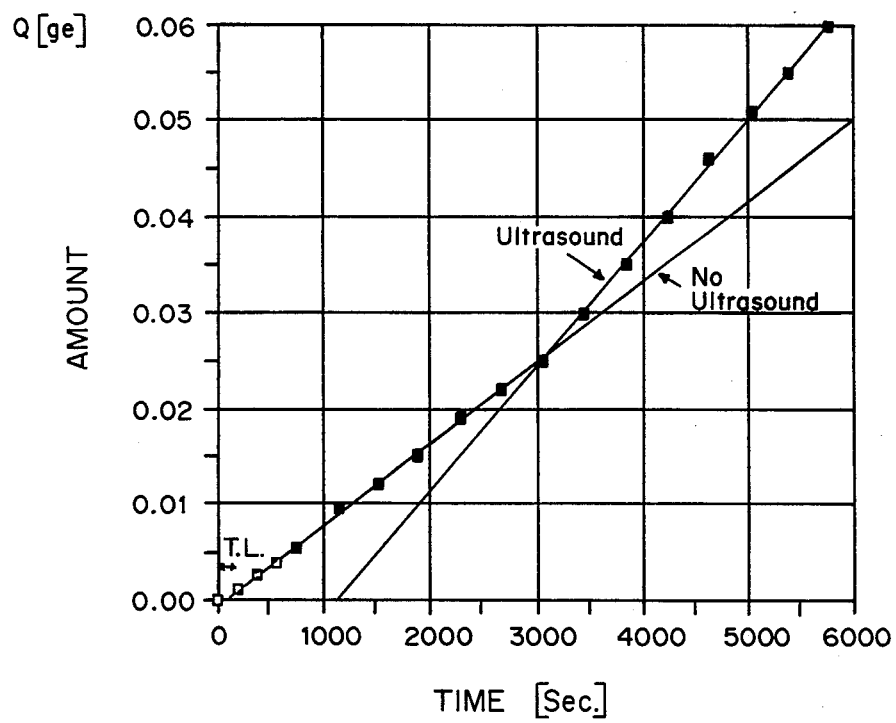
FIG. 1 is a graph of the effect of ultrasound on the amount of NaCl (grams) permeating through a cellulosic membrane as a function of time (seconds).

Ultrasound can be used to alter a molecule's relationship with its immediate environment, for example, a polymeric or biological membrane, or other molecules having the same composition, such as a protein aggregate.

The primary application of the present invention is to control the transport or permeability rate of molecules suspended or dissolved in a liquid media through a polymeric or biological membrane. One important practical application of this method is to increase the rate and selectivity of permeation of molecules through a membrane during kidney dialysis while maintaining control over the process. Equally important is the enhancement of the passage of oxygen through membranes into the blood in blood oxygenation devices. Another important commercial application is to increase the rate of separation processes, for example, during dialysis of protein solutions to change the ionic strength or to remove low molecular weight substances.

The distinguishing feature of the present invention is that it allows one to control permeation of molecules, especially large and/or biological molecules, through a membrane, whether selected for composition and structure, such as a polymeric membrane with a permeability within a discrete molecular weight range, or a biological membrane, which may vary enormously in composition, structure and permeability.

To date, ultrasound has been used only for enhancement of the permeation of a molecule through a membrane which is already permeable to the molecule. The present invention not only provides controlled movement, but it may be used to make a system in which a molecule moves through a membrane which was previously impermeable. For many situations, the molecule must move through the membrane at both a controlled rate and at a controlled concentration. Further, no one has used ultrasound to control the rate of movement of molecules during separation processes wherein it is desirable to move the different molecules at different rates.

The control of permeation is achieved by optimizing not only the ultrasound frequency, intensity, and length of exposure, but also the selection of the membrane and the solvent containing the molecules. In addition to composition, the membrane structure can be designed to respond to the ultrasound in a particular way. For example, the membrane may be made with a material which is stable over time in the solution containing the molecules to pass through the membrane or a composition may be used which degrades over time and/or as a function of exposure to the ultrasound.

Materials which can be used to make polymeric membranes include inorganic and organic polymers such as polyanhydrides, polymers of ethylenevinyl acetate, polypropylene, polyethylene, polyurethane, silicone, hydroxyethylmethacrylate, vinyl alcohol, polylactides, polyglycolides, polycaprolactone, lactic-glycolic copolymers, polyorthoesters, polyamides, polyacrylamide, agarose, carbohydrates and combinations of these materials.

Membranes may be single or multiple layer structures. Structure includes pore size, molecular configuration, crystallinity and thickness. Membranes may also be "biological membranes", such as skin, or artificially constructed complex membranes formed of phospholipids and other hydrophilic and hydrophobic compounds. The charge of the membrane may be used to affect permeability, as can the orientation of the ultrasound relative to the membrane.

The solution in which the molecule is suspended can be selected to affect the rate at which the molecules permeate the membrane in response to the ultrasound. A more viscous solution or one which attenuates the passage of sound may alter the effect of the ultrasound on the membrane and molecules. The solution may also cause the molecule to shrink or unfold, particularly where the molecule is a large protein, which will affect the passage of the molecule through the membrane as a function of the ultrasound. This can be accomplished by using a high salt solution or one containing a reducing compound. In general, penetration of a thicker solution requires a higher intensity of ultrasound. Using thinner (more shallow) solutions allows one to use a lower intensity of ultrasound. Less heat is generated at low intensity, as it is with pulsed instead of continuous ultrasound.

The ultrasound can be set at an intensity (defined as watts/cm$^2$) and frequency which results in degradation of the membrane or which produces only reversible changes in the membrane and/or molecules. The preferred frequency range is between 10 kHz and 20 MHz for most membranes and approximately 1 MHz and 3 MHz for biological membranes. The preferred intensity range is between 0.05 and 30 watts/cm$^2$ for most membranes and between 0.05 and three watts/cm$^2$ for biological membranes. In general, the duration of the exposure to ultrasound will be limited to avoid excessive temperature rises in either the solution containing the molecule or the membrane. A temperature rise of as little as 2° C. can cause irreversible damage to biological membranes. However, in some uses, irreversible damage to the membrane may be desirable. Most clinically approved ultrasound devices such as the Sonopuls 434 made by B. V. Enraf-Nonius Delft, Delft, Holland, have available frequencies of between 1 MHz and 3 MHz, continuous intensity of 0.05 to 2 W/cm$^2$ or pulsed intensity of 0.05 to 3 W/cm$^2$ (pulse repetition frequency of 100 Hz, pulse duration of 0.5, 1, or 2 ms), with a treatment timer of 0 to 15 minutes with ½ minute intervals.

The method of the present invention has a number of practical applications. For example, the ultrasound can be used to control movement of ionic species and low molecular weight peptides through dialysis membranes during artificial kidney dialysis. Under normal conditions, kidney dialysis may take several hours since the molecules move only as a function of the concentration gradient. Most commercially available kidney dialyzers are made with membranes of cellulose or cellulose derivatives. These units rely on a large surface area (about 1.2 m²) to minimize the required time for removal of waste products. The present invention provides enhancement of rate and/or selectivity of the kidney dialysis process. In a similar fashion, the application of ultrasound to membranes or the solution exposed to the membranes in a blood oxygenator can be used to enhance oxygenation, increasing the rate of passage of molecules through the membrane and/or which molecules pass through the membrane. It is important in these applications to control temperature rise and to minimize any damage to either the membrane or to the solutions, especially when the ultrasound is applied to whole blood.

Another application is in separation processes where the passage of molecules through membranes or molecular sieves can be enhanced by the use of ultrasound in conjunction with selection of the media. Membranes are used herein to mean structured membranes in a conventional sense as well as chromatographic or solid substrates for separations, such as Sepharose, polyacrylamide beads, polymethacrylate, agarose gels, ceramics, etc. The ultrasound can also be used to free or disperse molecules interspersed or entrapped within the membrane or chromatographic substrate.

"Molecules", as used herein, include chemical species, proteins, cofactors, inorganic compounds, nucleic acid sequences, saccharides, polymers and peptides. Enhancement of the permeability rate is particularly intended to apply to passage of large molecular weight molecules, defined as sugars, polymers and other molecules generally having a molecular weight in excess of 150 and extending up to a few million (nucleic acids and complex proteins).

Another embodiment of the present invention is in the separation of aggregated molecules in solution. For example, many biological molecules, including insulin produced by genetic engineering in bacteria, form physical complexes. This problem is aggravated by the high concentrations used in purification and packaging of these molecules. Rather than use chemical procedures or dilution, it is desirable to separate the molecules by a short exposure to ultrasound. The required frequency, exposure time, and intensity can be determined empirically by one skilled in the art for the conglomerate protein to be separated into its individual components.

In a similar fashion, ultrasound can be used to disperse clumps of cells or tissue. The primary limiting factors are temperature and the need to avoid cell damage.

This invention is further described by the following non-limiting examples.

EXAMPLE 1

The effect of ultrasound on permeation of small molecules through cellulosic membranes Applying ultrasound (20 kHz, 24 W in a 48 cm³ compartment duration) to a solution of NaCl in water, it is possible to calculate the change in permeability of a cellulosic membrane from the NaCl concentration, as compared to the concentration of NaCl not exposed to the ultrasound. The amount of salt is graphed versus time, as shown in FIG. 1, where $$\frac{P_{ultrasound}}{P_{no\ ultrasound}} = 1.5$$

The permeability of the membrane is definitely greater when exposed to the ultrasound.

EXAMPLE 2

Figure 2:
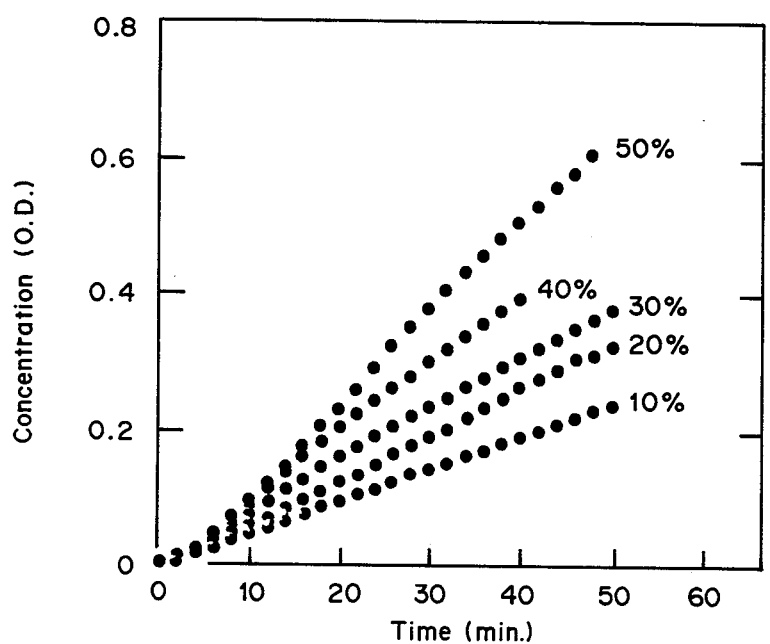
FIG. 2 is a graph of the permeability of BSA through Celgard microporous polypropylene membrane exposed to different ultrasound duty cycles (10%, 20%, 30%, 40%, 50%) versus time (min).

The effect of ultrasound on permeation of large biological molecules through cellulosic membranes FIG. 2 shows the increase in the concentration of Bovine Serum Albumin (66,000 mw) in the down stream compartment of a permeability cell. The upstream compartment was exposed continuously to ultrasound in a pulse mode (24 W in a 48 cm³ compartment). The duty cycle was changed from 10% to 50%. In the pulsed mode the rate is one pulse per second and can be varied from 10% on and 90% off, to 90% on and 10% off (1/10th of a second on and 9/10th of a second off, to 9/10th of a second on and 1/10th of a second off). The permeability is expressed by the slope of these curves. It can be seen that the slope is not only significantly affected by the ultrasound but can be controlled by the duty cycle.

EXAMPLE 3

Effect of ultrasound on the integrity of a large molecular weight biological compound Insulin solutions were exposed to ultrasound, as with the bovine serum albumin. No difference between the ultrasound treated and untreated insulin solutions could be detected when they were evaluated by HPLC, indicating that the ultrasound did not damage the integrity of the molecule.

EXAMPLE 4

Selective permeation of membranes using ultrasound

Figure 3:
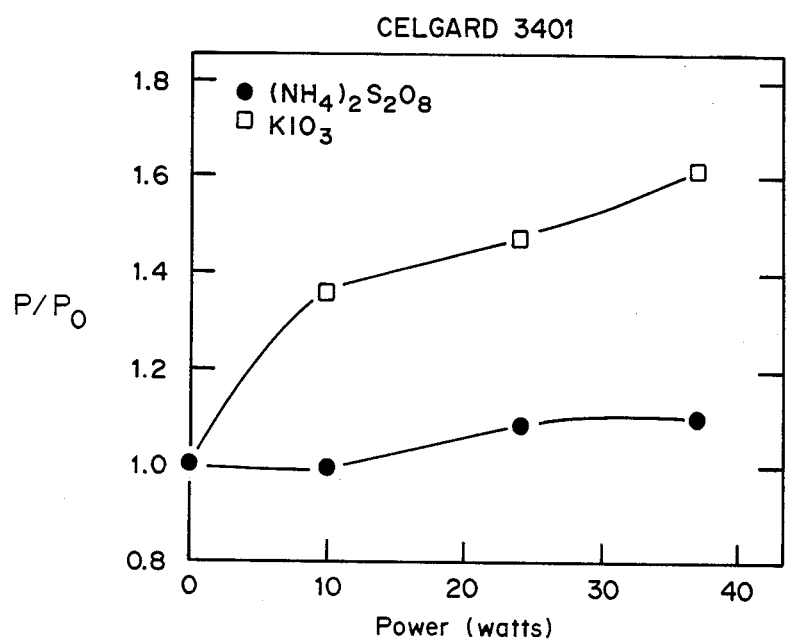
FIG. 3 is a graph of the ratio of permeabilities for two large molecular weight chemical compounds, $KIO_3$ and $(NH_4)_2S_2O_8$, through Celgard microporous polypropylene membranes, P/Po (permeability when exposed to the ultrasound/permeability when the membrane was not exposed to ultrasound) versus ultrasound power (watts).

FIG. 3 shows the effect of ultrasound power on the ratio of permeability when exposed to ultrasound to permeability while the ultrasound was turned off ($P/P_o$) The significant difference in enhancement of permeability of the membranes to these two complex inorganic molecules, $KIO_3$ and $(NH_4)_2 S_2O_8$, having very different molecular weights, demonstrates that ultrasound can, in addition to enhancement, improve membrane selectivity and therefore the membrane separation processes.

Although this invention has been described with reference to specific embodiments relating to the effect of ultrasound on the interaction of a molecule with its immediate molecular environment, especially transport or permeability through a membrane, it is understood that variations and modifications may occur to those skilled in the art. Such modifications and variations are intended to fall within the scope of the appended claims.

We claim:
1. A method comprising:
controlling transport of preselected species of molecules in a solution through a membrane, by, providing a membrane containing apparatus,
contacting a solution containing molecules with the membrane,
exposing the membrane containing apparatus to ultrasound, and adjusting the intensity, frequency and time of exposure of the ultrasound sufficient to selectively pass said preselected species of molecules through the membrane.

2. The method of claim 1 wherein the frequency and intensity of the ultrasound is limited to produce predominantly reversible changes in the molecules and membrane.

3. The method of claim 1 further comprising removing molecules interspersed within the membrane by exposing the membrane to ultrasound.

4. The method of claim 1 wherein the frequency of the ultrasound is between about 10 kHz and 20 MHz and the intensity of the ultrasound is between about 0.05 watt/cm$^2$ and 30 watts/cm$^2$.

5. The method of claim 4 wherein the ultrasound frequency is between approximately 1 MHz and 3 MHz and the intensity is between approximately 0.05 and 3 W/cm$^2$.

6. The method of claim 1 wherein the molecules are selected from the group of large molecular weight compounds consisting of proteins, cofactors, chemical compounds, nucleic acid sequences, saccharides, peptides, polymers and combinations thereof.

7. The method of claim 1 further comprising selecting a membrane composition and structure having a selective effect on the passage of the molecules in solution upon exposure to ultrasound.

8. The method of claim 7 wherein the membrane is selected to have a specific molecular weight cut off range.

9. The method of claim 7 wherein the membrane is selected from the group of organic, inorganic and biological polymer compositions consisting of polyanhydrides, ethylenevinyl acetate polymers, silicone, hydroxyethylmethacrylate, vinyl alcohol, polylactides, polyglyclolides, polycaprolactone, lactic glycolic copolymers, polyorthoesters, polyamides, agarose, carbohydrates, celluloses, polypropylene, polyethylene, polyurethanes, and combinations thereof.

10. The method of claim 1 further comprising selecting a membrane composition which degrades in response to the ultrasound.

11. The method of claim 10 further comprising selecting the frequency, intensity and time of exposure of the membrane to the ultrasound to increase the rate of degradation of the membrane.

12. The method of claim 1 further comprising altering the three dimensional structure of said molecules by selection of the solvent for the molecules.

13. The method of claim 12 further comprising selecting the solvent for the degree of attenuation of the ultrasound by the solvent.

14. The method of claim 1 wherein application of the ultrasound directly to the membrane alters the passage of the molecules through the membrane.

15. The method of claim 1 wherein application of the ultrasound to the solution alters passage of the molecules through the membrane.

16. The method of claim 1 wherein the passage of molecules through the membrane is enhanced.

17. A method for enhancing membrane dialysis comprising controlling transport of preselected species of molecules in a solution through a membrane, by, exposing a kidney dialysis apparatus to ultrasound at a frequency between about 10 KHz and 20 MHz and at an intensity of between about 0.05 and 30 W/cm$^2$, wherein the frequency and intensity of the ultrasound is limited to avoid irreversible damage to the membrane and blood.

18. A method for enhancing the oxygenation of blood comprising controlling transport of preselected species of molecules in a solution through a membrane, by, exposing a solution to be oxygenated in a membrane oxygenator device to ultrasound at a frequency between about 10 KHz and 20 MHz and an intensity of between about 0.05 and 30 W/cm$^2$, wherein the frequency and intensity of the ultrasound is limited to avoid irreversible damage to the membrane and solution.

19. A method for controlling the rate of a separation process comprising controlling transport of preselected species of molecules in a solution through a membrane, by, selecting a separation system medium and exposing the molecules to be separated to ultrasound in the medium, wherein the molecules move within the medium as a function of the frequency and intensity of the ultrasound.

20. The method of claim 19 further comprising selecting the separation mediums from the group of solid matrices consisting of agarose, sepharose, polymethacrylate, polyacrylamide, cellulose, ceramics and derivatives thereof.

* * * * *